(12) United States Patent
Duensing et al.

(10) Patent No.: US 10,877,113 B2
(45) Date of Patent: Dec. 29, 2020

(54) DETACHABLE CONNECTOR AND SPLITTABLE RF COIL HOUSINGS

(71) Applicant: KONINKLIJKE PHILIPS N.V., Eindhoven (NL)

(72) Inventors: George Randall Duensing, Eindhoven (NL); Olli Friman, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 789 days.

(21) Appl. No.: 14/787,522

(22) PCT Filed: Apr. 22, 2014

(86) PCT No.: PCT/IB2014/060904
§ 371 (c)(1),
(2) Date: Oct. 28, 2015

(87) PCT Pub. No.: WO2014/177975
PCT Pub. Date: Nov. 6, 2014

(65) Prior Publication Data
US 2016/0077172 A1 Mar. 17, 2016

Related U.S. Application Data

(60) Provisional application No. 61/818,477, filed on May 2, 2013.

(51) Int. Cl.
*G01R 33/34* (2006.01)
*G01R 33/36* (2006.01)
(Continued)

(52) U.S. Cl.
CPC .............. *G01R 33/34* (2013.01); *A61B 5/055* (2013.01); *G01R 33/34007* (2013.01);
(Continued)

(58) Field of Classification Search
CPC ............ H01R 2201/12; H01R 2201/04; H01R 2201/06; H01R 13/627; H01R 12/722;
(Continued)

(56) References Cited

U.S. PATENT DOCUMENTS 5,429,525 A * 7/1995 McCoy ................ H01R 13/627
439/352
5,502,387 A 3/1996 McGill
(Continued)

FOREIGN PATENT DOCUMENTS

WO WO 2004111670 A1 * 12/2004 ............. G01R 33/34
WO 20080073512 A2 6/2008

*Primary Examiner* — Keith M Raymond
*Assistant Examiner* — Patrick M Mehl (57) ABSTRACT

A local magnetic resonance (MR) radio frequency (RF) coil includes a plurality of housing sections that are separable and configured with mating surfaces that meet and engage each other to form an opening which receives a portion of subject anatomy for magnetic resonance imaging, a detachable connector, and a cable. Each housing section includes coil elements enclosed within each housing section which receive MR signals from the received portion of the subject anatomy, and external connectors connected to the coil elements co-located on an outside surface of each housing section and adjacent to the mating surfaces. The detachable connector connects to the external connectors of the housing sections. The cable conveys at least the received MR signals received by the coil elements.

10 Claims, 5 Drawing Sheets

(51) Int. Cl.
*A61B 5/055* (2006.01)
*G01R 33/3415* (2006.01)

(52) U.S. Cl.
CPC ....... *G01R 33/34084* (2013.01); *G01R 33/36* (2013.01); *G01R 33/3415* (2013.01); *G01R 33/3642* (2013.01)

(58) Field of Classification Search
CPC ............... H01R 13/114; H01R 13/6478; F15B 13/0857; G01R 33/34007; G01R 33/34084; G01R 33/36; G01R 33/3642; G01R 33/3415; G01R 33/20; A61B 5/055
See application file for complete search history.

(56) References Cited

U.S. PATENT DOCUMENTS

| | | | |
|---|---|---|---|
| 5,594,337 A | 1/1997 | Boskamp | |
| 5,664,568 A | 9/1997 | Srinivasan | |
| 6,141,580 A * | 10/2000 | Hayashi | G01R 33/34046 600/422 |
| 6,316,941 B1 * | 11/2001 | Fujita | G01R 33/34046 324/318 |
| 6,692,311 B1 * | 2/2004 | Kamei | H01R 9/2458 439/218 |
| 7,465,196 B2 * | 12/2008 | Duarte | H01R 13/567 439/394 |
| 2003/0185003 A1 * | 10/2003 | Laukhuf | H01R 31/02 362/652 |
| 2007/0090840 A1 | 4/2007 | Chmielewski | |
| 2007/0152667 A1 * | 7/2007 | Schubert | G01R 33/34046 324/318 |
| 2009/0030305 A1 | 1/2009 | Hoogeveen | |
| 2009/0189610 A1 * | 7/2009 | Li | G01R 33/34046 324/322 |
| 2011/0040174 A1 * | 2/2011 | Driemel | G01R 33/34007 600/422 |
| 2012/0153956 A1 | 6/2012 | Driemel | |
| 2012/0306494 A1 * | 12/2012 | Yang | G01R 33/3664 324/318 |
| 2013/0033265 A1 * | 2/2013 | Chiodo | G01R 33/30 324/321 |

* cited by examiner

DETACHABLE CONNECTOR AND SPLITTABLE RF COIL HOUSINGS

CROSS REFERENCE TO RELATED APPLICATIONS

This application is a U.S. national phase application of International Application No. PCT/I82014/060904, filed on Apr. 22, 2014, which claims the benefit of U.S. provisional Application Ser. No. 61/818,477 filed on May 2, 2013 and is incorporated herein by reference.

The following relates generally to magnetic resonance medical imaging. It finds particular application in conjunction with magnetic resonance (MR) local radio-frequency (RF) coils and will be described with particular reference thereto. However, it will be understood that it also finds application in other usage scenarios and is not necessarily limited to the aforementioned application.

Local RF coils or surface coils are positioned closely adjacent or touching a patient in an MR scanner. Some local coils have an internal cavity or opening to receive an imaged portion of subject anatomy such as a chest, head, shoulder, wrist, forearm, knee, foot, etc. Local coils with splittable housings allow a coil to be separated into halves or sections. The sections allow greater freedom in ergonomic design and patient comfort. For example, a split knee coil allows the sections to be separated and mated around a knee of a subject. The contours of the housing surface close to the subject can be matched more closely with the shape of the knee. With a non-splittable housing, the subject slides the foot and lower leg through an opening large enough to accommodate the foot and lower leg. The opening large enough to accommodate the foot and lower leg increases the size of the opening and changes the contours which place the coil elements or antenna further away from the portion of the subject anatomy being imaged.

A typical design for a splittable housing includes halves which mate and each half includes galvanic electrical connections, e.g. pins, which connect to sockets in the other section. The electrical connections complete coil loops, provide DC power to halves, and carry received MR signals to an attached cable. For example, a mating edge of a lower and upper section typically includes multiple electrical connections on each side. An electrical connection connects coil loop segments between the halves to form complete loops. A local coil can include multiple coil elements. Typically, the coil edge of each section includes a series of electromechanical connectors which mate to connect the sections electrically and mechanically. The cable, often permanently affixed to the lower section, provides for communication of the received MR signals from the local coil to the system, provides power from the system to circuitry such as analog-to-digital converters and amplifiers of the local coil, and/or provides power for RF pulses if the local coil is configured to operate as a transmit coil. Having the cable connected to one section while the section is being fitted to the subject can add complexity or extra bulk to the effort by the healthcare practitioner in positioning the split housing.

Repeated use of the split housing wears the electrical connectors between the two halves, which can become damaged, unreliable, and/or add noise to the signals. For example, a lower half in a head coil is placed beneath the head the subject. The upper half is placed over the face of the subject and fitted to the lower half. As the upper half is being position, the healthcare practitioner will naturally take care in positioning over the face of the subject, but will likely involve some lateral or sliding movement to fit the upper to the lower half of the split coil housing which wears and can damage the connectors. Additionally when removing the upper housing after imaging, care may be taken with regard to the subject face, but an upward pull to separate the two halves may not be a uniform upward motion. Some designs attempt to reinforce or recess the connectors to minimize wear and possible damage, but reinforcement or recess adds to the cost and to the complexity of fitting the sections together.

The following discloses a new and improved detachable connector and splittable RF coil housings which addresses the above referenced issues, and others.

In accordance with one aspect, a local magnetic resonance (MR) radio frequency (RF) coil includes a plurality of housing sections that are separable and configured with mating surfaces that meet and engage each other to form an opening which receives a portion of subject anatomy for magnetic resonance imaging, a detachable connector, and a cable. Each housing section includes coil elements enclosed within each housing section which receive MR signals from the received portion of the subject anatomy, and external connectors connected to the coil elements co-located on an outside surface of each housing section and adjacent to the mating surfaces. The detachable connector connects to the external connectors of the housing sections. The cable conveys at least the received MR signals received by the coil elements.

In accordance with another aspect, A method of MR imaging with a local RF coil includes physically mating housing sections of the local RF coil around a portion of a subject anatomy, each section including a mating surface which meets and engages other sections to form an opening which receives the portion of the subject anatomy, coil elements enclosed within each housing section which receive MR signals, and external connectors connected to the coil elements co-located on an outside surface of each housing section and adjacent to the mating surface. A detachable connector is attached to the external connectors of the housing sections.

In accordance with another aspect, a local MR RF coil includes a plurality of housing sections that are separable and which receives a portion of subject anatomy for MR imaging. Each housing section includes mating surfaces that engage other sections to form an internal opening, and coil elements which when mated spatially overlap with coil elements of the mated section to capacitively couple, and receive MR signals.

One advantage is split coil housings which separate mating of sections from the connecting of power and communication connections.

Another advantage is ease in positioning coil housing sections without a cord.

Another advantage resides in the reduction of wear on the electrical connectors during positioning of the sections on a subject.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
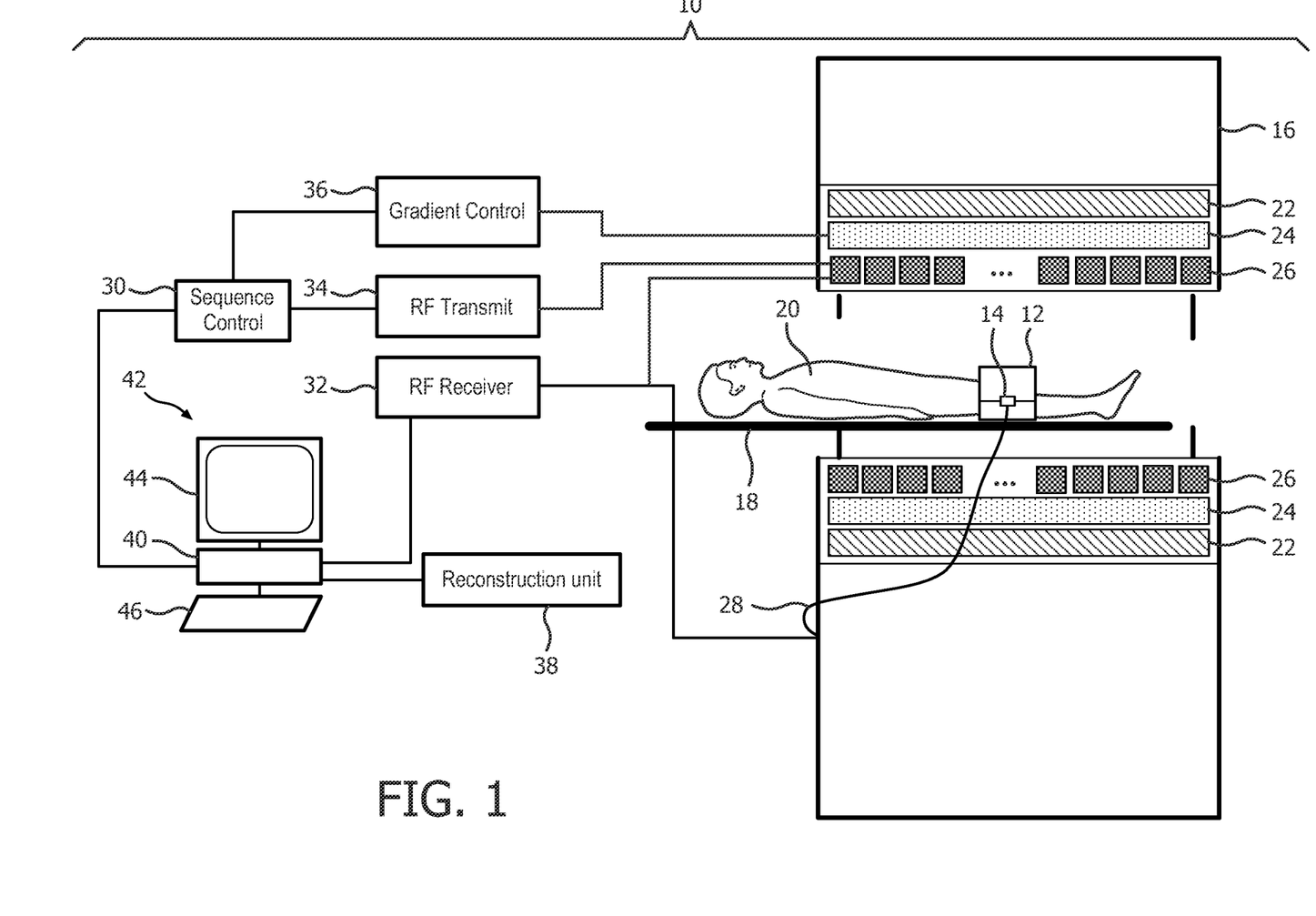
FIG. 1 schematically illustrates an embodiment of an MR system with a detachable connector attached to a splittable local MR RF coil.

With reference to FIG. 1, an embodiment of an MR system 10 (shown in diagrammatic partial cross-section) with a local splittable MR RF coil 12 and a detachable connector 14 is schematically illustrated. The local RF coil 12 is embodied as a splittable knee coil and the detachable connector 14 are shown in an attached configuration. The MR system 10 includes a MR scanner 16 illustrated in partial cross section with a static $B_0$ main field such as a horizontal bore scanner, open system scanner, c-type scanner, vertical field scanner, and the like. The MR scanner includes a subject support 18 such as a horizontal bed or couch which supports a subject 20 and moves the subject into the MR scanner bore and static field during imaging. The MR scanner 16 includes a main magnet 22 which generates the static main field ($B_0$) such as a horizontal main field. The MR scanner further includes one or more gradient coils 24 for applying gradient fields for manipulating resonance in the tissues of the subject. The MR scanner includes one or more RF coils 26 which generate RF pulses to excite magnetic resonance in the subject 20 such as a transmit mode and can receive resonance signals from the subject in a receive mode. In some embodiments the local RF coil 12 performs both transmit and receive functions, in which case the whole-body RF coil 26 is optionally omitted.

The local RF coil 12 includes one or more coils or coil elements which receive resonance signals from the subject in the receive mode and in some embodiments can operate in the transmit mode. The detachable connector 14 is connected with a cable 28 can be used interchangeably with other splittable coils. The connector can be uniform across multiple coils. For example, the detachable connector 14 can be connected to other knee coils and to other splittable coils with the same detachable connector receiver such as head, wrist, foot, and the like.

The system 10 includes a sequence controller 30 and a RF receiver unit 32. The sequence controller controls the operation of the imaging sequence which includes a RF transmitter unit 34 controlling the operation of the RF coils 26 and/or the local RF coil 12 with the detachable connector 14. A gradient controller 36 controls the operation of the gradient coils 24. The communication between the controlling unit and the corresponding coils can be wired or wireless. The RF transmitter unit 34 works cooperatively with the local coil 12 when the local coil is configured as a transmit/receive coil. The RF receiver 32 receives RF data, e.g. MR signals as from the cable with the connector detachably attached to the local RF coil 12 indicative of the magnetic resonance excited in the tissue of the subject. The coil elements can be located close to the subject anatomy being imaged because the split coil can be narrowed to the subject anatomy. For example, the opening for the knee is shaped to the knee anatomy and due to the split opening does not require a larger opening to accommodate a foot or calf to pass through the opening. Power can be supplied to the splittable coil through the cable 28. The cable 28 can transmit the MR signals electrically or optically.

A reconstruction unit 38, embodied as a configured processor such as a processor 40 of a system console 42, receives the demodulated MR signals from the RF receiver 32 and reconstructs one or more images. The system console 42 includes the electronic processor or electronic processing device 40, a display 44 which displays the reconstructed image, power supply operational status, menus, panels, and user controls. At least one input device 46 inputs healthcare practitioner selections. The system console 42 can be a desktop computer, a laptop, a tablet, a mobile computing device, a smartphone, and the like. The input device 46 can be a keyboard, a mouse, a microphone, and the like. The reconstruction unit is suitably embodied by an electronic data processing device, such as the electronic processor or electronic processing device 40 of the system console 42, or by a network-based server computer operatively connected with the system console 42 by a network, or so forth. Moreover, the reconstruction technique is suitably implemented using a non-transitory storage medium storing instructions (e.g., software) readable by an electronic data processing device and executable by the electronic data processing device.

Figure 2:
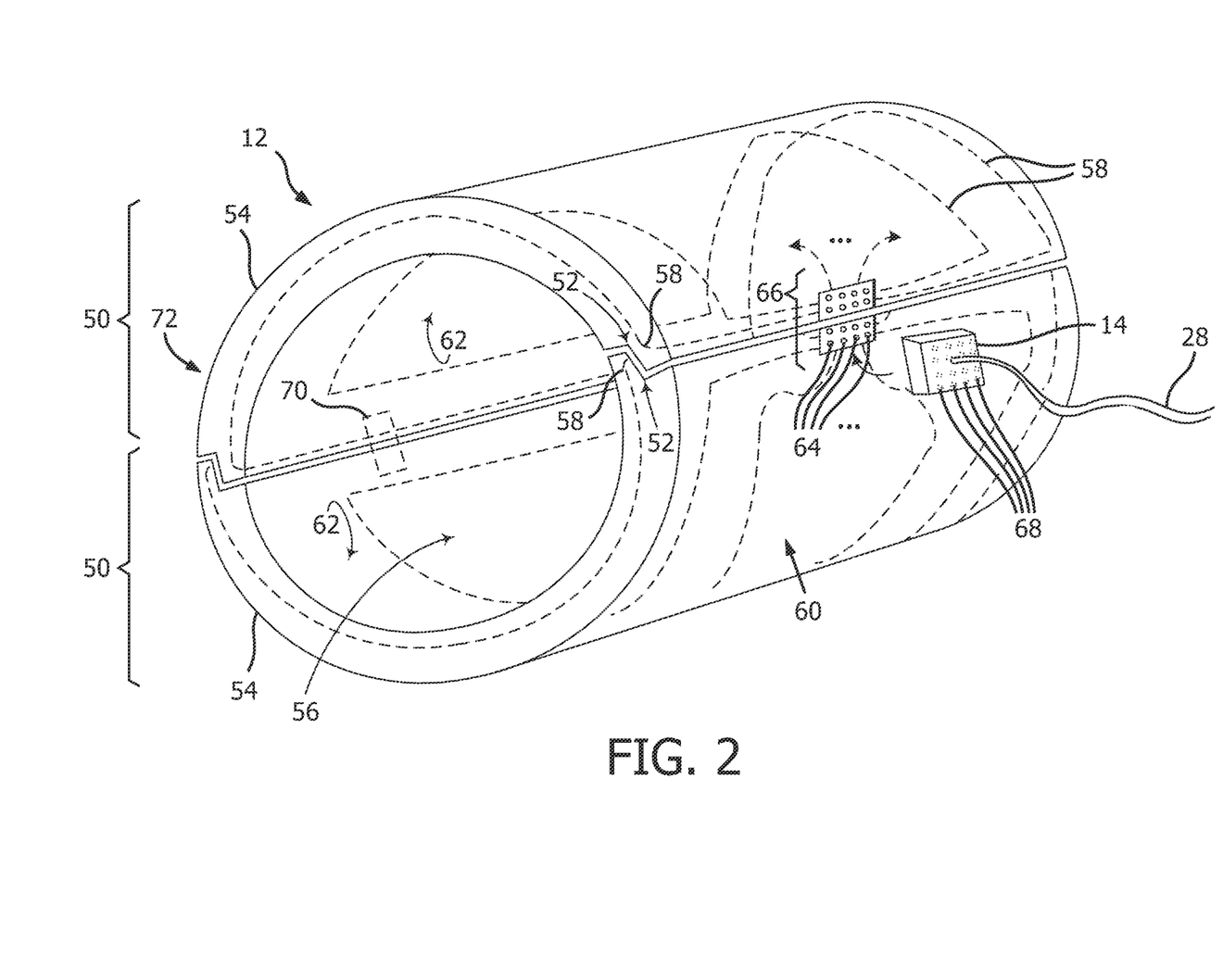
FIG. 2 schematically illustrates in perspective one embodiment of a splittable local MR RF coil and the detachable connector in a detached configuration.

With reference to FIG. 2, one embodiment of a splittable local MR RF coil 12 and the detachable connector 14 in a detached configuration is illustrated in perspective. The splittable local MR RF coil 12 includes sections 50 which are separable. The combining and splitting of the coil sections 14 is separate from connections for power and transmission of MR signals. With the separation, the combining and splitting of the coil sections does not wear on the connectors for power and data transmission. The sections 50 are each configured with mating surfaces 52 of a housing 54 that meet and engage each other to form an opening 56 which receives a portion of subject anatomy, e.g., knee, forearm, elbow, head, shoulder, etc. The housing 54 includes an outside or exterior surface 60 and an inside or interior surface 62 which form a smooth surface across sections in a mated configuration. The interior surface refers to the housing surface closest to the subject anatomy. The opening 56 receives the region of interest for imaging.

Each section 50 includes a housing 54 which encloses coil elements 58. The edges of the housing and the coil elements spatially overlap when the sections are mated such that coil elements are capacitively coupled. With the mating surfaces 52 providing partial overlap circumferentially between sections, and coil elements located in the overlapping sections, the coil elements can be capacitively or inductively coupled across the mating surfaces. The coil elements are connected with external connectors 64 which are co-located on the exterior surface 60 of each housing section and adjacent to the mating surfaces. The external connectors can be configured into a receiving block 66. The receiving block receives the detachable connector 14 which includes a complement of connectors 68 shown in phantom which connect to the external connectors 64 of the sections 50. A predetermined format and number of connectors provides a unified connection between the detachable connector and the external connectors 64 or receiver 66. The coil elements receive power from the cable via the connectors and transmit MR signal data via the connectors to the cable. The external connectors 64 and complement of connectors 68 include electrical connectors and/or optical connectors.

The split coil housing can include one or more latching mechanisms 70 shown in phantom, which physically latches the sections together in a closed configuration. The latching mechanisms are located along the exterior surface 60 adjacent the mating surfaces 52. The latch can be incorporated into the detachable connector, along the exterior surface on the same side as the receiver 66, and/or an opposite side 72.

Figure 3:
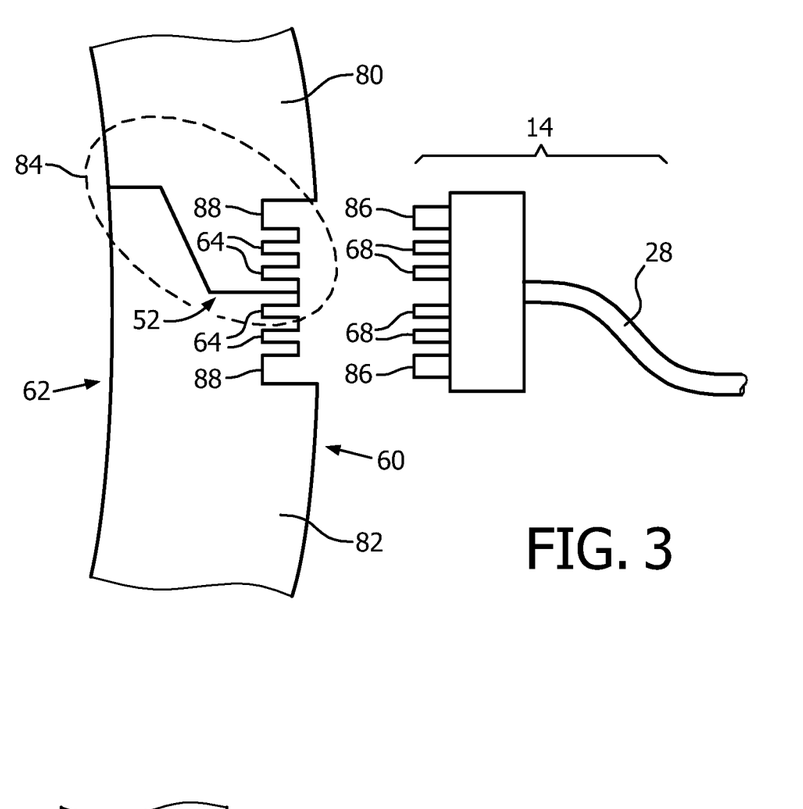
FIG. 3 diagrammatically illustrates in cross section one embodiment of the detachable connector and a receiver of the splittable local MR RF coil.

With reference to FIG. 3, one embodiment of the detachable connector 14 and the receiver 66 of the splittable local MR RF coil 12 is diagrammatically illustrated in cross section. A first section 80 and a second section 82 meet and engage along the mating surface 52. The mating surface includes an overlap 84 between the sections. The first section 80 and the second section 82 each include external connectors 64 which receive the connectors 68 of the detachable connector 14.

The detachable connector 14 can include a latching mechanism 86 which latch to latching elements 88 of the other sections. For example, the detachable connector includes a rigid skirt 86 around the connectors 68 which extends from the detachable connector. The skirt can protect the connectors 68. The connectors 68 can be male connectors while the external connectors 64 of the sections can be female connectors. Alternatively, both male and female connectors can be provided on all sections. The latching elements 88 of the sections are shown as a recessed portion surrounding the external connectors and which receives the rigid skirt and holds the sections together. Other latching mechanisms are contemplated such as posts, levers, mechanical locks, Velcro™, and the like.

Figure 4A:
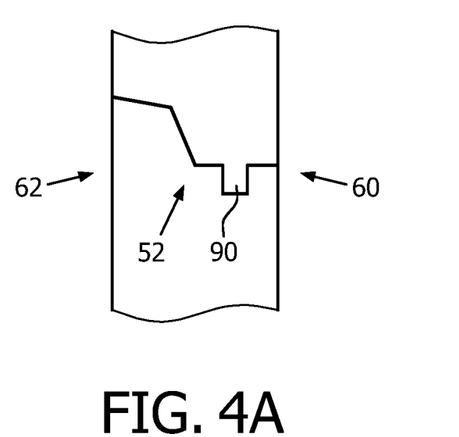
FIGS. 4A-4B diagrammatically illustrates exemplary physical attachment mechanisms of mating surfaces.
Figure 4B:
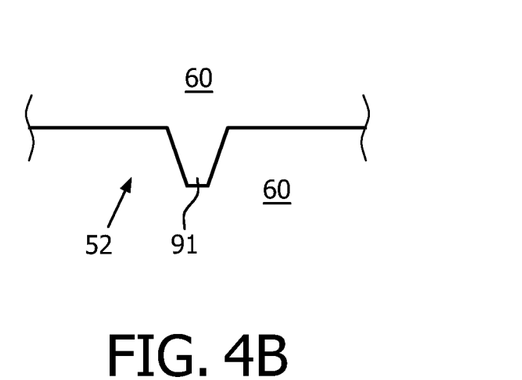

With reference to FIGS. 4A and 4B, exemplary physical attachment mechanisms 90 of mating surfaces 52, are diagrammatically illustrated. FIG. 4A shows one embodiment in partial cross section with mating surfaces 52, interior surfaces 62 and the exterior surfaces 62 of two sections. The mating surface includes the physical attachment mechanism 90 in the form of a pin on a mating surface of a first section which mates with a bore on a second section. Flex spring elements may be used to increase frictional connection between the socket and bore. FIG. 4B shows another embodiment as a partial front view of the exterior surface of mating sections. The mating surfaces 52 include a physical attachment mechanism 91 such as a notch. The physical attachment mechanism 90, 91 of FIGS. 4A and 4B provide a mechanism which facilitates lateral alignment, but allows the coil sections to be split with force or motion from a healthcare practitioner which pulls the sections apart with opposing force.

Figure 5A:
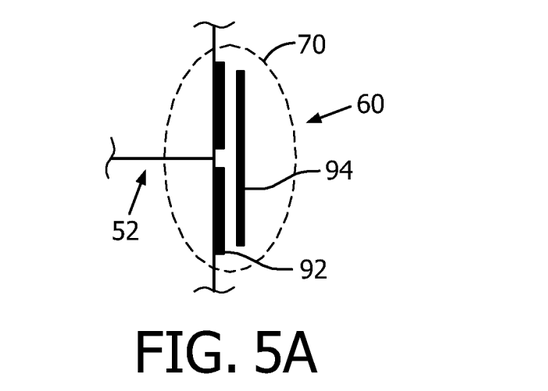
FIGS. 5A-5C diagrammatically illustrates in cross section exemplary latching mechanisms of coil sections.
Figure 5B:
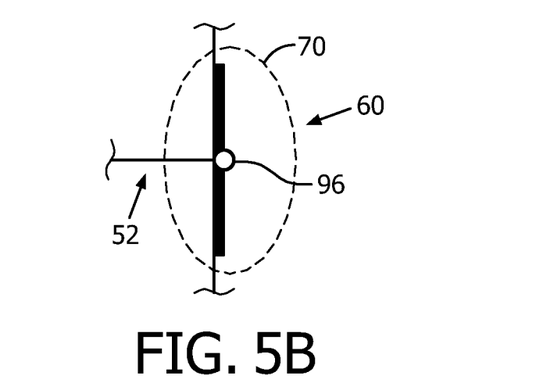
Figure 5C:
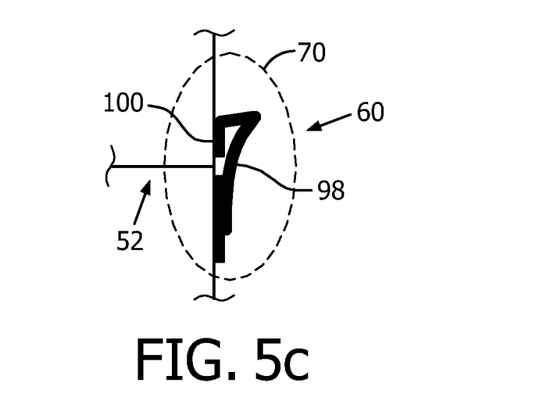

With reference to FIGS. 5A-5C, exemplary latching mechanisms 70 of coil sections are diagrammatically illustrated in cross section. A fabric hook and loop fastener, e.g. Velcro™, is shown in FIG. 5A. Each section includes a first surface 92 such as loops which receives a second surface 94 such as hooks and latch together to hold the sections together. Alternatively, a first section includes the first surface and a second section includes a second surface which extends to latch to the first surface. FIG. 5B shows a hinge mechanism 96 which allows the sections to pivot open to receive the subject anatomy, while remaining connected at the hinge. In another embodiment, the hinge pin can be removable. FIG. 5C shows a hook as a latching mechanism. One section includes the hook 98 and the mating section includes a hook engaging element 100 to which the hook latches.

Figure 6:
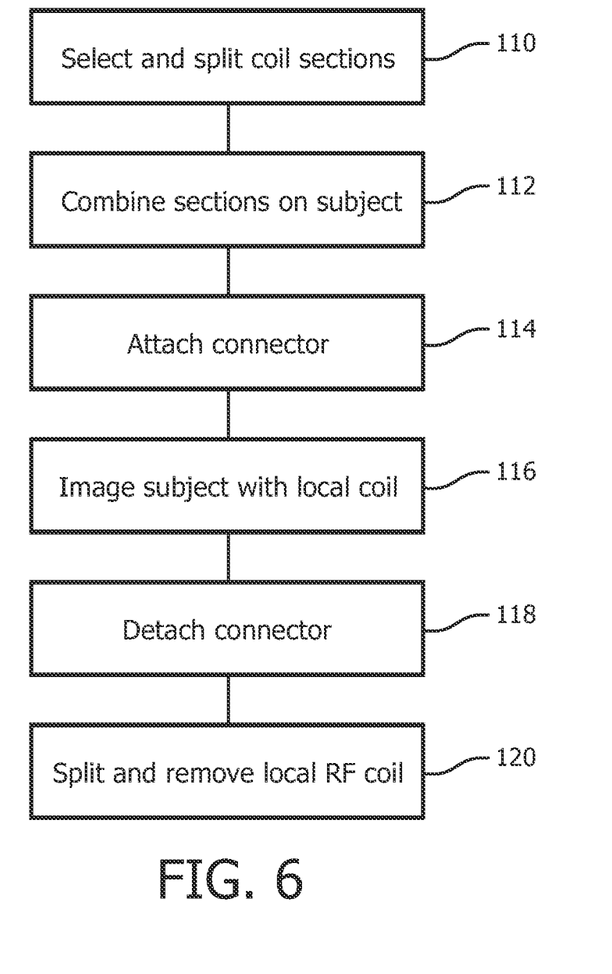
FIG. 6 flowcharts a method of using an embodiment of the detachable connector and local split MR RF coil.

FIG. 6 flowcharts a method of using an embodiment of the detachable connector and local split MR RF coil. In a step 110, a split coil is selected and the coil housing sections separated. In a step 112, the coil sections are physically mated around a portion of subject anatomy. For example, a first coil section is place under a knee and a second coil section placed over the front or top of the knee and mated with the first coil section to surround the knee. The mating surfaces of the sections meet and engage each other to form the opening which holds the imaged portion of subject anatomy. The mating can include engaging physical attachment mechanisms such as pins or notches in the mating surfaces. The mating includes overlap in housing sections which include coil elements enclosed within each housing section. The coil elements partially overlap circumferentially around the mated sections and during imaging receive MR signals. External connectors connected to the coil elements are co-located on an outside surface of each housing section and adjacent to the mating surface. For example, the external connectors can be included in a receiver formed when the sections are mated. Latching mechanisms can be engaged between sections to latch the sections together such as hinges, hooks, fabric hook and loop fasteners, and the like.

The detachable connector 14 is attached to the sections in a step 114. The detachable connector connects to the external connectors of the housing sections and includes a cable which conveys the received MR signals. The detachable connector 14 can be selected from among a number of detachable connectors of the same connector format. The external connectors can form a receptical which receives the detachable connector. The detachable connector supplies power and/or receives MR signals. The attachment of the detachable connector establishes electrical connections for power and/or communication connections for transmission of MR signals across the connectors to the cable. The communications can include electrical and/or optical communications. The detachable connector can include a latching mechanism. The latching mechanism can be engaged when the detachable connector is inserted into the receptical.

The portion of subject anatomy is imaged using the local split coil in a step 116. The step includes moving the subject with the local split coil on the subject support into the static field of the MR scanner. The step includes the coil elements receiving MR signals which are conveyed through the external connectors to the detachable connector which includes the complementary connectors connected to wire and/or optical fiber included in the cable. The transmitted MR signals are received by the RF receiver 32. The step includes reconstructing the received MR signals into an image by the reconstruction unit 46.

In a step 118, the detachable connector 14 is detached from the local split coil 12. The detachment includes disconnecting the power and/or communications link. Detachment can include releasing the latching mechanism of the detachable connector. The latching mechanisms between the coil sections are released in a step 120 and the coil sections removed from the subject. For example, a split knee coil with a latching mechanism that includes a hinge can be opened and removed from the subject. In another example with a split knee coil a latching mechanism of fabric hook and loops and an physical engagement mechanism of pins, the fabric is separated to release the latching mechanism, and the sections lifted apart with upward force to separate an upper section from a lower section. Each section is removed from the subject.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A local magnetic resonance (MR) radio frequency (RF) coil comprising:
   a plurality of housing sections including a first housing section and a second housing section that are configured to be separable and configured with mating surfaces that meet and engage each other, the housing sections in an engaged configuration define a volume configured to receive a portion of subject anatomy for magnetic resonance imaging, the housing sections including:
      coil elements enclosed within each housing section and configured to receive MR signals from the received portion of the subject anatomy,
      external connectors connected to the coil elements to convey received MR signals therefrom, the external connectors including a first external connector located on the first housing section adjacent its mating surface and a second external connector co-located on an outside surface of the second housing section adjacent to its mating surface and when the mating surfaces engage each other, the first and second external connectors are adjacent each other,
   a single detachable connector configured to concurrently (a) connect mechanically to the first and second external connectors and releasably holding the first and second external connectors and the mating surfaces of the first and second housing sections together and (b) convey the received MR signals from the first and second external connectors, a cable connected with the single detachable connector and configured to convey at least the received MR signals received by the coil elements from the first and second external connectors and the single detachable connector to an RF receiver,
   wherein the single detachable connector and the first and second external connectors include pins and sockets configured to releasably interconnect.

2. The local MR RF coil according to claim 1, wherein the mating surfaces include a partial overlap around the circumference of each housing section and the coil elements such that the coil elements capacitively couple across the mating surfaces.

3. The local MR RF coil according to claim 1, wherein the mating surfaces mate to provide a smooth surface across mated sections on both an interior surface adjacent the volume and an exterior surface.

4. The local MR RF coil according to claim 1, wherein the mating surfaces include a physical engagement and alignment mechanism.

5. The local MR RF coil according to claim 1, wherein the external connectors and the single detachable connector include electrical connectors.

6. The local MR RF coil according to claim 1, wherein the external connectors and the single detachable connector include optical connectors.

7. A method of MR imaging with a local RF coil, the method comprising:
   physically mating two housing sections of the local RF coil around a portion of a subject anatomy, each of the two housing sections including:
      a mating surface which meets and engages a mating surface of another section to form a volume configured to receive the portion of the subject anatomy,
      coil elements enclosed within each housing section which receive MR signals, and
      an external connector connected to the coil elements of each of the two housing sections and co-located on an outside surface of each of the two housing sections and adjacent to the mating surface such that when the mating surfaces met the external connectors are adjacent to each other;
   attaching a single detachable connector to the external connectors of the two housing sections, attaching the single detachable connector with the external connectors (a) holds the two housing sections together by holding the adjacent external connectors together and (b) connects the coil elements via the external connectors and the single detachable connector with an RF receiver;
   imaging the subject anatomy with the local RF coil including conveying MR signals received by the coil elements of the mated housing sections through external connectors, the single detachable connector, and a cable attached to the single detachable connector to the RF receiver;
   reconstructing the conveyed MR signals into an image of the portion of subject anatomy;
   detaching the single detachable connector from the external connectors; and
   separating the housing sections after detachment of the single detachable connector from the external connectors.

8. The method according to claim 7, wherein physically mating includes:

partially overlapping coil elements around the circumference of each section to capacitively couple the overlapped coil elements.

9. The method according to claim 7, wherein attaching the single detachable connector establishes electrical connections between the external connectors and the detachable connector.

10. A local magnetic resonance (MR) radio frequency (RF) coil including:
- a pair of housing sections configured to separate to facilitate receipt of a portion of the subject anatomy and mate to define a volume for MR imaging of the received anatomy portion, each housing section including:
  - a mating surface that engages the mating surface of the other of the pair of sections,
  - coil elements configured to receive MR signals from the received anatomy portion,
  - a pin/socket external connector mounted on an outside surface of each housing section adjacent to the mating surface such that the pin/socket external connectors of a pair of matingly disposed housing sections are disposed adjacent each other; and
- a detachable pin/socket connector which electrically and mechanically connects to both of the external connectors of the pair of housing sections and (a) latches the pair of housing sections mechanically and (b) electrically connects the coil elements to a cable which conveys the received MR signals.

\* \* \* \* \*